(12) United States Patent
Nakashima

(10) Patent No.: US 6,757,410 B1
(45) Date of Patent: Jun. 29, 2004

(54) FINGERPRINT VERIFICATION SYSTEM AND FINGERPRINT VERIFYING METHOD

(75) Inventor: Yutaka Nakashima, Tokyo (JP)

(73) Assignee: NEC Electronics Corporation, Kanagawa (JP)

( * ) Notice: Subject to any disclaimer, the term of this patent is extended or adjusted under 35 U.S.C. 154(b) by 535 days.

(21) Appl. No.: 09/598,962

(22) Filed: Jun. 22, 2000

(30) Foreign Application Priority Data

Jun. 24, 1999 (JP) ........................................ 1999/178539

(51) Int. Cl.[7] .............................................. G06K 9/00
(52) U.S. Cl. ...................... 382/124; 382/218; 382/289; 360/5.83
(58) Field of Search ................................ 382/124, 126, 382/209, 278, 125, 129, 127, 218, 197, 280, 216, 289; 356/71, 369, 138; 340/5.83

(56) References Cited

U.S. PATENT DOCUMENTS

| | | | | |
|---|---|---|---|---|
| 4,208,651 A | * | 6/1980 | McMahon | 382/125 |
| 4,936,680 A | | 6/1990 | Henkes et al. | |
| 5,040,223 A | * | 8/1991 | Kamiya et al. | 382/126 |
| 5,067,162 A | * | 11/1991 | Driscoll, Jr. et al. | 382/126 |
| 5,261,088 A | * | 11/1993 | Baird et al. | 382/127 |
| 5,493,621 A | * | 2/1996 | Matsumura | 382/125 |
| 5,953,443 A | * | 9/1999 | Hiratsuka et al. | 340/5.83 |
| 6,134,340 A | * | 10/2000 | Hsu et al. | 382/124 |
| 6,188,780 B1 | * | 2/2001 | Nakayama | 382/124 |

FOREIGN PATENT DOCUMENTS

| | | |
|---|---|---|
| EP | 0 862 131 A2 | 9/1998 |
| JP | 61-175865 | 8/1986 |
| JP | 62-272378 | 11/1987 |
| JP | 02-270076 | 11/1990 |
| JP | 04-043469 | 2/1992 |
| JP | 05-242224 | 9/1993 |
| JP | 06-162174 | 6/1994 |
| JP | 08-263631 | 10/1996 |
| JP | 10-293833 | 4/1998 |
| JP | 10-124667 | 5/1998 |

\* cited by examiner

*Primary Examiner*—Jayanti K. Patel
*Assistant Examiner*—Sheela Chawan
(74) *Attorney, Agent, or Firm*—Foley & Lardner LLP (57) ABSTRACT

A fingerprint verification system for verifying input fingerprint data with pre-registered reference fingerprint data is disclosed, the reference fingerprint data being data containing the fingerprint data, the pre-designated rotated angles, and the rotated order thereof, the system comprising a rotation data and reference fingerprint data storing portion for storing the reference fingerprint data.

2 Claims, 9 Drawing Sheets

FINGERPRINT VERIFICATION SYSTEM AND FINGERPRINT VERIFYING METHOD

BACKGROUND OF THE INVENTION

1. Field of the Invention

The present invention relates to a fingerprint verification system and a fingerprint verifying method for authenticating a person, in particular, to a fingerprint verification system and fingerprint verifying method using rotated angles of fingerprint data and a pre-designated rotated order thereof.

2. Description of the Related Art

In a conventional fingerprint verification system, when a fingerprint is registered and verified, a fingerprint of one finger is verified with all entries of fingerprint data that have been registered.

Mizukura Isao has disclosed "Individual Identifying Device" in Japanese Patent Laid-Open Publication No. 61-175865 (hereinafter this related art reference is referred to as first related art reference). According to the first related art reference, an input device such as a ten key pad for successively inputting registration numbers is disposed. When fingerprint data is registered, it is verified with successively assigned registration numbers that only the person who registers his or her fingerprint data knows. When the person is authenticated, he or she inputs the order of fingers and the assigned registration numbers. Thus, only fingerprint data corresponding to the registration numbers is read from the storing portion.

Suzuki Takao, Kawasaki Koji, and Kamiya Toshiharu have disclosed "Detection Device for Fingerprint Picture Rotational Amount" in Japanese Patent Laid-Open Publication No. 4-43469 (hereinafter, this related art reference is referred to as second related art reference). According to the second related art reference, a fingerprint is detected as a reference picture. The detected reference picture is overlaid with a registered fingerprint picture in such a manner that their center points match. In this state, angle differences of feature points of these pictures are detected. An angle difference that is most frequently takes place in those is output as a rotated angle of the reference picture. Thus, according to the second related art reference, the relative rotated angle of a verification picture and a registered picture can be accurately obtained without need to perform complicated calculations. As a result, according to the second related art reference, the fingerprint verification device can be compactly structured.

Igaki Seigo and Niizaki Taku have disclosed "Fingerprint Collating Device" in Japanese Patent Laid-Open Publication No. 5-242224 (hereinafter, this related art reference is referred to as third related art reference). Since fingerprints have two major features of "unique for each person" and "no change in lifetime", it is said that they are the most effective means for identifying individuals. According to the third related art reference, a fingerprint picture is read and a feature picture is extracted therefrom as a window picture. The extracted picture is registered as an entry of a fingerprint dictionary. A rotating amount of the input verification picture against the center position of the fingerprint of the input reference picture is detected. The fingerprint reference picture and the window picture are verified. Thus, according to the third related art reference, even if fingerprint data is input in the state that the finger is rotated against the fingerprint data that has been registered, the person can be accurately identified.

Yokoyama Ken has disclosed "Fingerprint Matching Method" in Japanese Patent Laid-Open Publication No. 6-162174 (hereinafter, this related art reference is referred to as fourth related art reference). According to the fourth related art reference, for improving the system security, corresponding to conditions (such as a rotation and a distortion) of fingerprint data that is input, a search range of a plurality of verifying windows is adjusted. Thus, according to the fourth related art reference, the verification success ratio is improved.

Nakajima Hiroshi and Kobayashi Koji have disclosed "Pattern Collating Device" in Japanese Patent Laid-Open Publication No. 10-124667 (hereinafter, this related art reference is referred to as fifth related art reference). According to the fifth related art reference, even if there is a rotational deviation between a registered pattern and a reference pattern, they are verified. To do that, the pattern verification device according to the fifth related art reference comprises a registering Fourier pattern data generating means, a reference Fourier pattern data generating means, a combining means, an amplitude suppressing means, and a verifying means. The registering Fourier pattern data generating means performs an N-th dimensional discrete Fourier transforming process for a plurality of N-th dimensional patterns that are an N-th dimensional pattern as the registered pattern and N-th dimensional patterns of which the registered N-th dimensional pattern is rotated by predetermined angles. The reference Fourier pattern data generating means performs the N-th dimensional discrete Fourier transforming process for the N-th dimensional patterns and generates reference Fourier N-th dimensional patterns. The combining means successively reads and combines the registered Fourier N-th dimensional rotated patterns with the reference Fourier N-th dimensional pattern. The verifying means verifies the registered pattern and the reference pattern corresponding to the intensity of a verifying component area of the combined Fourier N-dimensional pattern.

However, the above-described related art references have the following problems.

According to the above-described related art reference, as a first problem, the primary object is to verify fingerprint data. In those related art references, information other than fingerprint data is not used. Thus, in comparison with a system using other information (such as rotated angles and a rotated order) as well as fingerprint data, the security level is low.

As a second problem, since registration numbers are used, a registration number input device such as a ten key pad as same as ten fingers is required.

According to the above-descried related art references, a finger is rotated so that registered fingerprint information matches reference fingerprint information. In other words, according to those related art references, a finger is rotated not from a view point of improving the security level.

SUMMARY OF THE INVENTION

The present invention is made from the above-described point of view. An object of the present invention is to provide a fingerprint verifying method and a fingerprint verification system using information (such as rotated angles and a rotated order) as well as fingerprint data so as to further improve the security level.

A first aspect of the present invention is a fingerprint verifying method for authenticating a person, comprising the steps of (a) inputting fingerprint data, (b) registering the input fingerprint data, (c) registering predetermined rotated angles of the fingerprint data and the rotated order thereof along with the input fingerprint data, and (d) verifying the input fingerprint data with the reference fingerprint data.

A second aspect of the present invention is a fingerprint verification system for verifying input fingerprint data with pre-registered reference fingerprint data is disclosed, the reference fingerprint data being data containing the fingerprint data, the pre-designated rotated angles, and the rotated order thereof, the system comprising a rotation data and reference fingerprint data storing portion for storing the reference fingerprint data.

According to the fingerprint verifying method and the fingerprint verification system of the present invention, it becomes difficult to forge a fingerprint and commit a fraud using a forged fingerprint.

Figure 1:
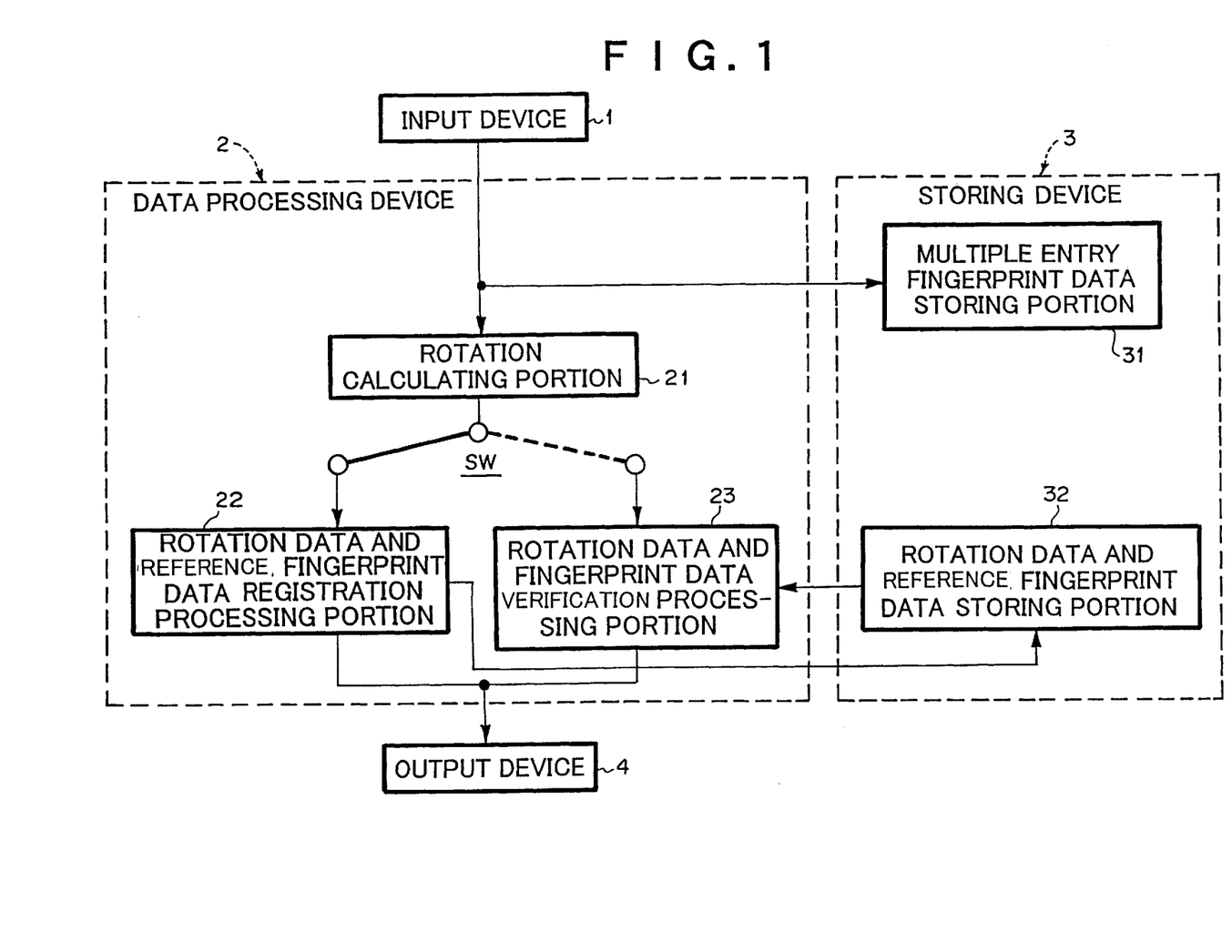
FIG. 1 is a block diagram showing the structure of a first embodiment of the present invention.

With reference to FIG. 1, in the fingerprint verification system according to the present invention, a rotation calculating portion 21 calculates rotated angles and a rotated order of a plurality of entries of a fingerprint that are rotated by a plurality of any angles. The plurality of entries of the fingerprint are input from an input device 1. A rotation data and reference fingerprint data registration processing portion 22 stores the reference fingerprint data, the rotated order thereof, and the rotated angles thereof to a rotation data and reference fingerprint data storing portion 32. A rotation data and fingerprint data verification processing portion 23 verifies the rotated angles, the rotated order, and the fingerprint data of input data with those of registered data.

In such a manner, a fingerprint of a person to be verified is rotated at a plurality of desired angles. The rotated angles and the rotated order thereof are verified with fingerprint data and the correlated data is registered. When a fingerprint data verification process is performed, fingerprint data is input at the registered rotated angles in the registered rotated order. Thus, even if fingerprint data is forged, it is difficult to commit a fraud using the forged fingerprint data. Thus, the reliability of the system is improved.

These and other objects, features and advantages of the present invention will become more apparent in light of the following detailed description of a best mode embodiment thereof, as illustrated in the accompanying drawings.

DESCRIPTION OF PREFERRED EMBODIMENTS

Next, with reference to the accompanying drawings, embodiments of the present invention will be described.

[First Embodiment]

(1) Description of Structure

FIG. 1 shows the structure of a fingerprint verification system according to the first embodiment of the present invention. Referring to FIG. 1, the fingerprint verification system comprises an input device 1, a data processing device 2, a storing device 3, and an output device 4. The input device 1 is for example a compact fingerprint scanner. The data processing device 2 operates corresponding to a program. The storing device 3 stores information such as fingerprint information. The output device 4 is for example a displaying device and/or a printing device.

The storing device 3 is composed of a main storing device and a peripheral storing device. The main storing device is for example a DRAM or a flash memory. The peripheral memory is for example a hard disk or an MO disk. The storing device 3 has a multiple entry fingerprint data storing portion 31 and a rotation data and reference fingerprint data storing portion 32.

The multiple entry fingerprint data storing portion 31 stores a plurality of entries of fingerprint data used for registering and verifying fingerprint data that is input from the input device 1.

The rotation data and reference fingerprint data storing portion 32 stores registered reference fingerprint data, rotated angles thereof, and a rotated order thereof.

The data processing device 2 comprises a rotation calculating portion 21, a rotation data and reference fingerprint data registration processing portion 22, a rotation data and fingerprint data verification processing portion 23, and a switch SW. The switch SW selectively connects the rotation calculating portion 21 to one of the rotation data and reference fingerprint data registration processing portion 22 and the rotation data and fingerprint data verification processing portion 23.

The rotation calculating portion 21 calculates the rotated angles and the rotated order of fingerprint data stored in the multiple entry fingerprint data storing portion 31. When the fingerprint data registering process is performed for the input fingerprint data with the predetermined rotated angle and rotated order, the calculated rotated angles and rotated order are supplied to the rotation data and reference fingerprint data registration processing portion 22 along with the input fingerprint data. When the fingerprint data verifying process is performed, the input fingerprint data and fingerprint data that has been registered are supplied to the rotation data and fingerprint data verification processing portion 23.

The rotation data and reference fingerprint data registration processing portion 22 generates reference fingerprint data using the fingerprint data that is supplied from the rotation calculating portion 21 and stores the generated reference fingerprint data to the rotation data and reference fingerprint data storing portion 32 along with the rotated angles and the rotated order. Thereafter, the rotation data and reference fingerprint data registration processing portion 22 outputs the registered results to the output device 4.

The rotation data and fingerprint data verification processing portion 23 verifies the rotated angles, the rotated order, and the input fingerprint data that are supplied from the rotation calculating portion 21 with those stored in the rotation data and reference fingerprint data storing portion 32 and outputs the verified results to the output device 4.

The input device 1 is for example a fingerprint scanner that directly reads input fingerprint data with a photoelectric converting device or a semiconductor sensor that is as small as the size of a finger and supplies the scanned data as fingerprint picture data to the multiple entry fingerprint data storing portion 31. The fingerprint input portion has a detecting area and a physical space for which the user can rotate his or her finger.

The output device 4 is for example a displaying device and/or a printing device. The displaying device is for example an LCD display or a CRT monitor. The printing device is for example a printer. The output device 4 may output data to an external storing device. The output device 4 displays and/or prints verified results of whether or not the input fingerprint data matches pre-registered fingerprint data.

(2) Description of Operation

Figure 2:
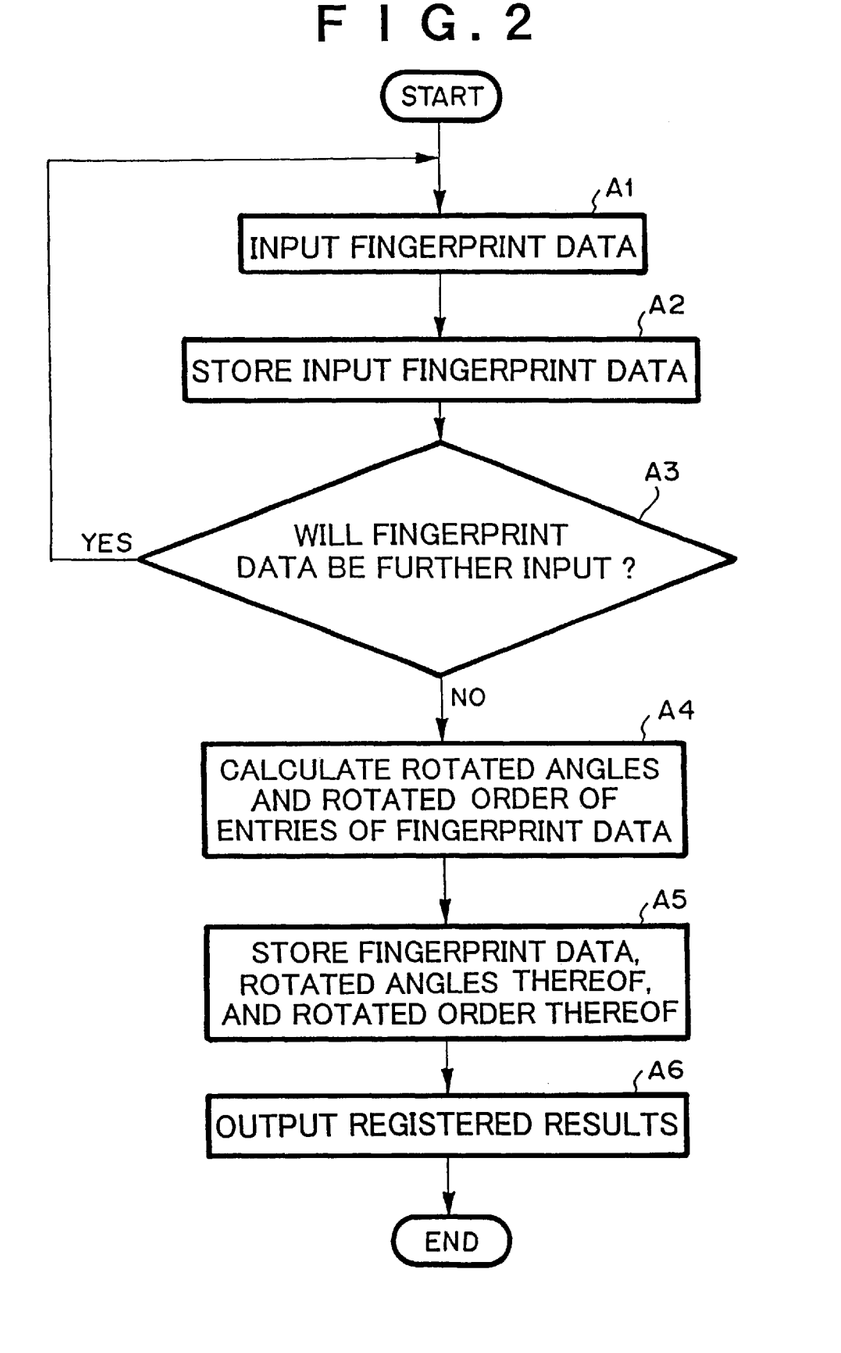
FIG. 2 is a flow chart showing a fingerprint data registering process according to the first embodiment of the present invention.
Figure 3:
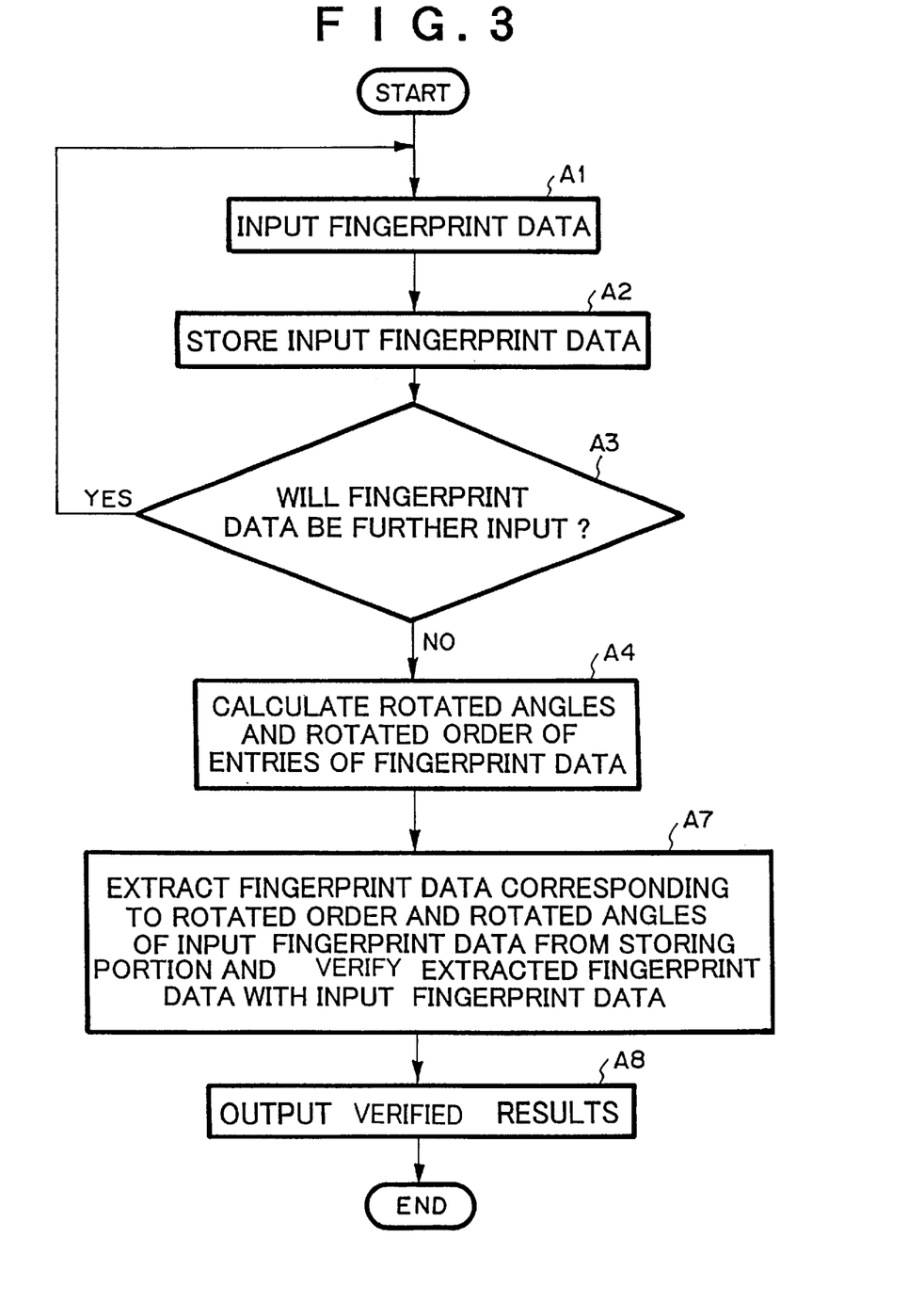
FIG. 3 is a flow chart showing a fingerprint data verifying process according to the first embodiment of the present invention.

Next, with reference to FIGS. 1, 2, and 3, the overall operation of the first embodiment will be described in detail. FIGS. 2 and 3 are flow charts showing processes of the first embodiment of the present invention.

With reference to FIGS. 1 and 2, a fingerprint data registering process according to the first embodiment of the present invention will be described. Fingerprint data rotated at a plurality of angles that only the person knows is input with the input device 1. The input fingerprint data that was rotated at the designated angles is stored to the multiple entry fingerprint data storing portion 31 (at steps A1, A2, and A3 shown in FIG. 2). Thereafter, the rotation calculating portion 21 calculate the rotated angles of the input fingerprint data and the rotated order thereof (at step A4).

The rotated angles of the fingerprint data are detected by the system disclosed in for example "Detection Device for Fingerprint Picture Rotational Amount" in Japanese Patent Laid-Open Publication No. 4-43469. In other words, as feature points of a fingerprint picture, a top point having the sharpest angle of a rotated pattern and at least one of ends of fingerprint wrinkle are designated. The rotated angles of the designated feature points against the center point of the picture area are detected in the range from 0 to 180 degrees. Fingerprint data is successively input at designated rotated angles in the designated rotated order. In this case, the person can freely select the number of rotations of the fingerprint data. The rotated order is calculated corresponding to the order of the rotated angles of the fingerprint.

The switch SW connects the rotation calculating portion 21 and the rotation data and reference fingerprint data registration processing portion 22. The rotation data and reference fingerprint data registration processing portion 22 stores the rotated angles, the rotated order, and the reference fingerprint data that have been obtained at step A4 to the rotation data and reference fingerprint data storing portion 32 (at step A5). The reference fingerprint data (of which feature points have been extracted) is obtained with one finger. In this example, a verification system having high sensitivity as disclosed in Japanese Patent Laid-Open Publication No. 62-2272378 may be used.

In the system, with a contrast checking means, it is determined whether or not a fingerprint picture has been stored in a frame buffer. The fingerprint picture supplied from a picture input means is stored to the frame buffer. Thereafter, the pitch width of rise lines of the fingerprint is measured by a pitch width measuring means. When the pitch width is equal to or larger than 5 pixels, a small area dividing means divides the picture data into small areas each of which is composed of 10×10 pixels. When the pixel width is smaller than 5 pixels, the small area dividing means divides the picture data into small areas each of which is composed of 8×8 pixels. The directional angle of a rise line of each small area is calculated by a directional angle calculating means. The calculated directional angle data is registered by a registering means. The reference data and the registered data are verified by a verifying means so as to determine whether or not they are the same. After the fingerprint data has been registered, the registered result is output to output device 4 (at step A6).

Next, with reference to FIGS. 1 and 3, a fingerprint data verifying process for verifying input fingerprint data with fingerprint data registered in the rotation data and fingerprint data verification processing portion 23 will be described.

Since steps A1 to A4 shown in FIG. 3 are the same as those shown in FIG. 2, for simplicity, their description is omitted. The switch SW connects the rotation calculating portion 21 to the rotation data and fingerprint data verification processing portion 23. The rotation data and fingerprint data verification processing portion 23 extracts fingerprint data corresponding to the rotated angles and the rotated order of the input fingerprint data that have been calculated by the rotation calculating portion 21 from the rotation data and reference fingerprint data storing portion 32 and verifys the input fingerprint data with the registered fingerprint data (at step A7). In the fingerprint data verifying process, the same verification system as the fingerprint data registering process may be used (namely, the verification system disclosed in Japanese Patent Laid-Open Publication No. 62-272378 is used).

In other words, as described above, with a contrast checking means, it is determined whether or not a fingerprint picture has been stored in a frame buffer. The fingerprint picture supplied from a picture input means is stored to the frame buffer. Thereafter, the pitch width of rise lines of the fingerprint is measured by a pitch width measuring means. When the pitch width is equal to or larger than 5 pixels, a small area dividing means divides the picture data into small areas each of which is composed of 10×10 pixels. When the pixel width is smaller than 5 pixels, the small area dividing means divides the picture data into small areas each of which is composed of 8×8 pixels. The directional angle of a rise line of each small area is calculated by a directional angle calculating means. The calculated directional angle data is registered by a registering means. The reference data and the registered data are verified by a verifying means so as to determine whether or not they are the same. After the fingerprint data has been registered, the registered result is output to output device 4 (at step A8).

Next, a real example of the process will be described. First, it is assumed that fingerprint data of a right index finger is successively rotated at angles 0, −45 and +45 in the rotated order. In this case, the fingerprint data is input with three rotated angles of 0, −45 and +45 in the order. Thus, the fingerprint data of the right index finger is stored to the multiple entry fingerprint data storing portion 31. At step A4 shown in FIG. 2, the rotated angles 0, −45 and +45 and the rotated order thereof are calculated. The rotated angles, the rotated order, and the input fingerprint data are stored to the rotation data and reference fingerprint data storing portion 32 (at step A5).

Figure 4:
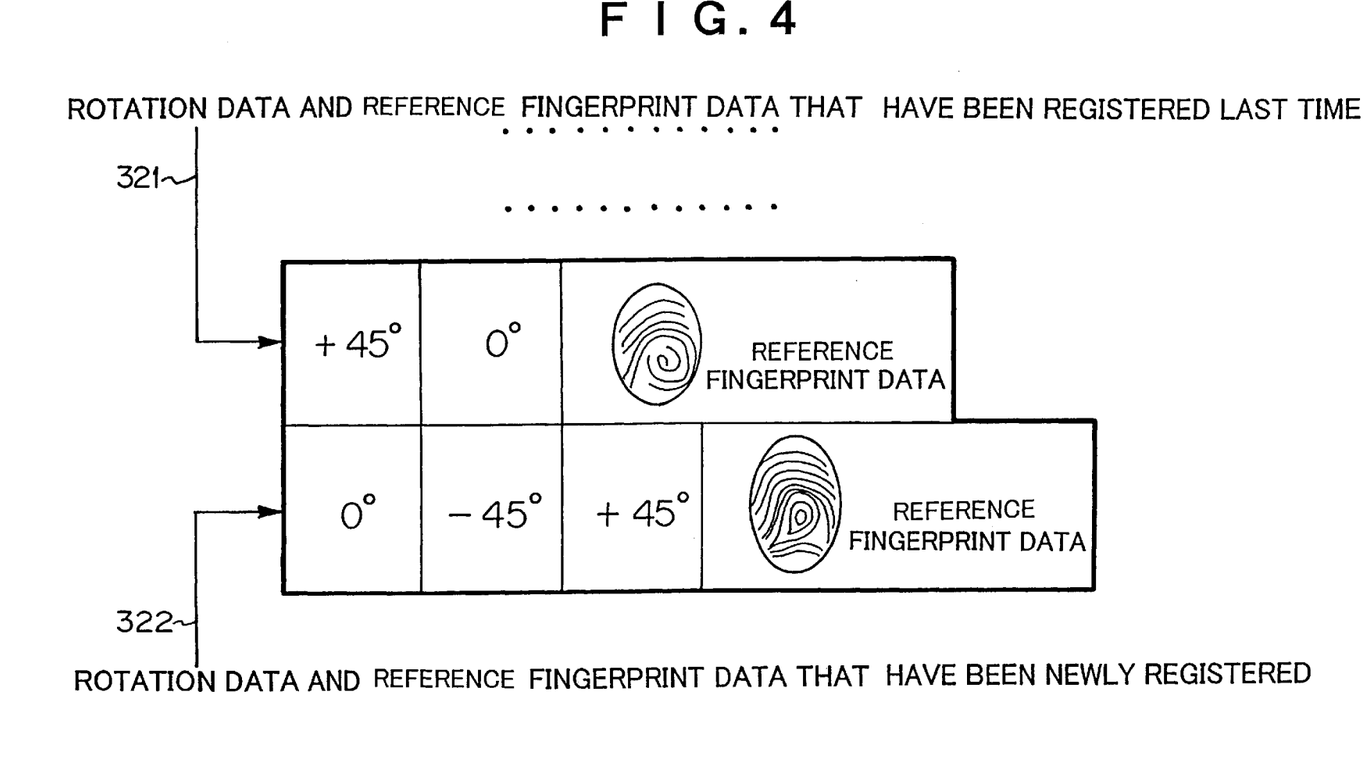
FIG. 4 is a schematic diagram showing images of fingerprints that have been registered and verified according to the first embodiment of the present invention.
Figure 9:
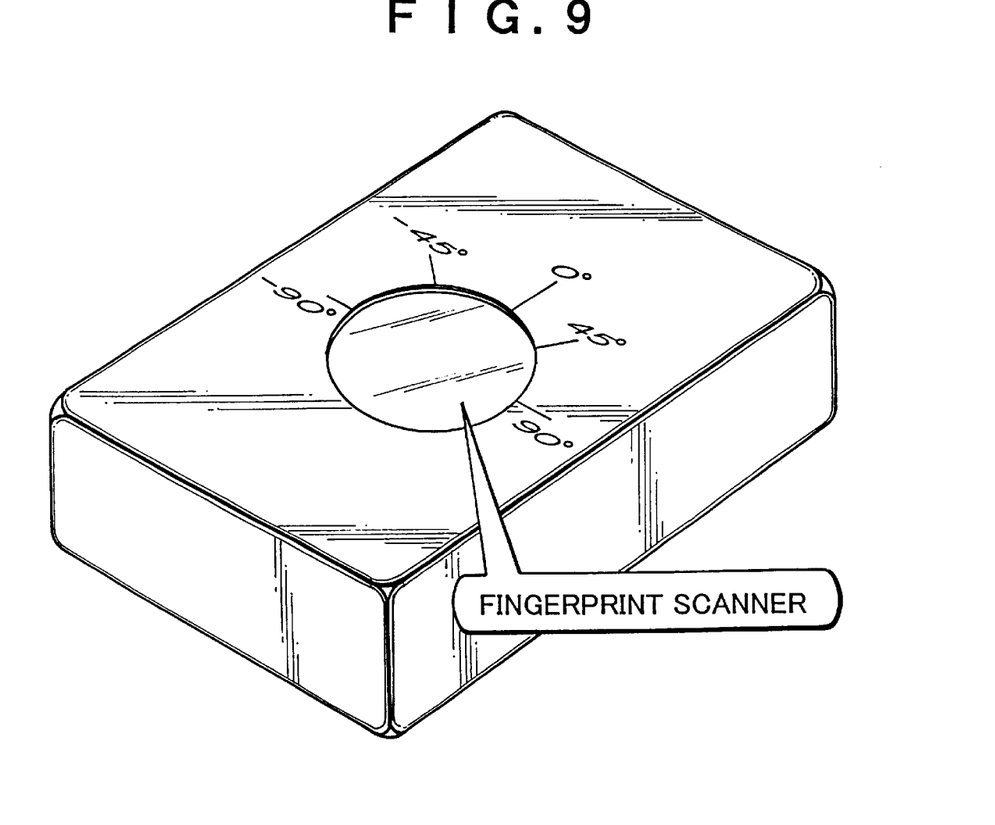
FIG. 9 is an external view showing a fingerprint scanner according to the present invention.

FIG. 4 shows an image of rotation data and reference fingerprint data 321 that had been registered in the rotation data and reference fingerprint data storing portion 32 and an image of rotation data and reference fingerprint data 322 that has been newly registered. When the fingerprint data verifying process is performed, assuming that fingerprint data of a right index finger rotated at angles 0, −45 and +45 in the order is input, fingerprint data rotated at angles 0, −45, and +45 in the order is extracted from the rotation data and reference fingerprint data storing portion 32. The fingerprint data that is extracted from the rotation data and reference fingerprint data storing portion 32 is verified with the input fingerprint data (at step A7). In this example, it is assumed that when the deviation of rotated angles of two patterns is in a predetermined range for example ±5, they are the same. Alternatively, as shown in FIG. 9, when the fingerprint data input device has angle guides of −90, −45, 0, 45, and 90, fingerprint data can be easily input at any of desired rotated angles.

In the first example, fingerprint data of one finger was input. However, it should be noted that the number of fingers with which fingerprint data is input is not limited to one. For example, after fingerprint data of one finger rotated at desired angles in a desired rotated order is input, when fingerprint data of another finger rotated at desired angles in a desired order, the security level can be further improved.

At step A7 shown in FIG. 3, fingerprint data is filtered with rotated angles thereof and a rotated order thereof. In contrast, rotated angles and a rotated order data may be filtered with fingerprint data. In addition, fingerprint data for extracting feature points is not limited to that of one finger.

[Second Embodiment]

(1) Description of Structure

Next, with reference to the accompanying drawings, a second embodiment of the present invention will be described.

Figure 5:
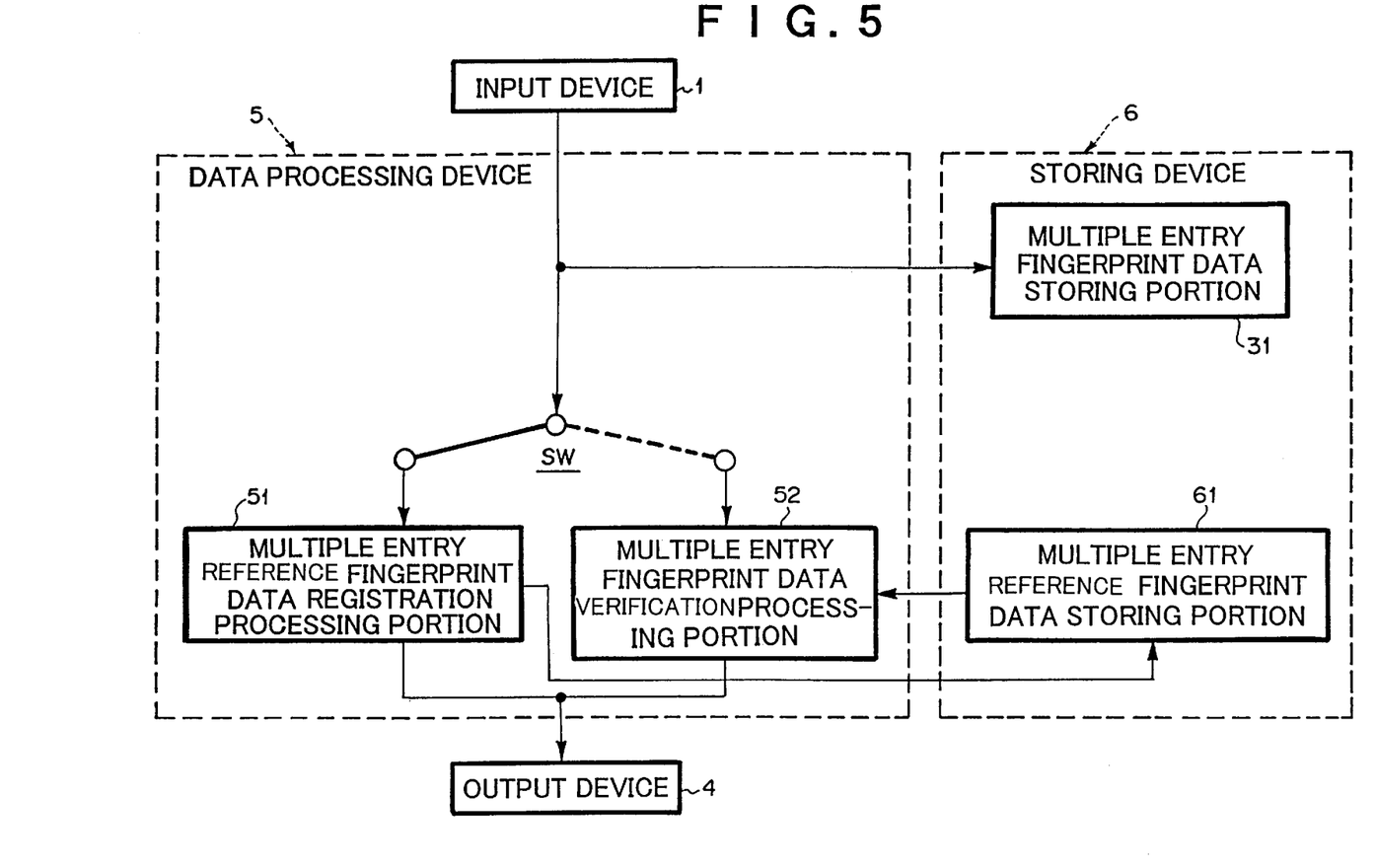
FIG. 5 is a block diagram showing the structure according to a second embodiment of the present invention.

FIG. 5 is a block diagram showing the structure of the second embodiment of the present invention. The difference between the first embodiment shown in FIG. 1 and the second embodiment shown in FIG. 5 is in that the data processing device 5 has a storing device 6 shown in FIG. 5 instead of the storing device 3 shown in FIG. 1. For simplicity, in FIG. 5, similar portions to those in FIG. 1 are denoted by similar reference numerals and their description is omitted.

The storing device 6 comprises a multiple entry fingerprint data storing portion 31 and a multiple entry reference fingerprint data storing portion 61.

The multiple entry fingerprint data storing portion 31 shown in FIG. 5 is equivalent to the multiple entry fingerprint data storing portion 31 shown in FIG. 1. The multiple entry reference fingerprint data storing portion 61 stores a plurality of entries of fingerprint data that have been registered.

The data processing device 5 comprises a multiple entry reference fingerprint data registration processing portion 51 and a multiple entry fingerprint data verification processing portion 52.

The multiple entry reference fingerprint data registration processing portion 51 generates reference fingerprint data (of which feature points have been extracted) with all entries of fingerprint data stored in the multiple entry fingerprint data storing portion 31 and stores them to the multiple entry reference fingerprint data storing portion 61. Thereafter, the multiple entry reference fingerprint data registration processing portion 51 outputs the registered results to the output device 4.

The multiple entry fingerprint data verification processing portion 52 verifies a plurality of entries of fingerprint data that have been input with fingerprint data that has been stored in the multiple entry reference fingerprint data storing portion 61. Thereafter, the multiple entry fingerprint data verification processing portion 52 outputs the verified results to the output device 4.

(2) Description of Operation

Figure 6:
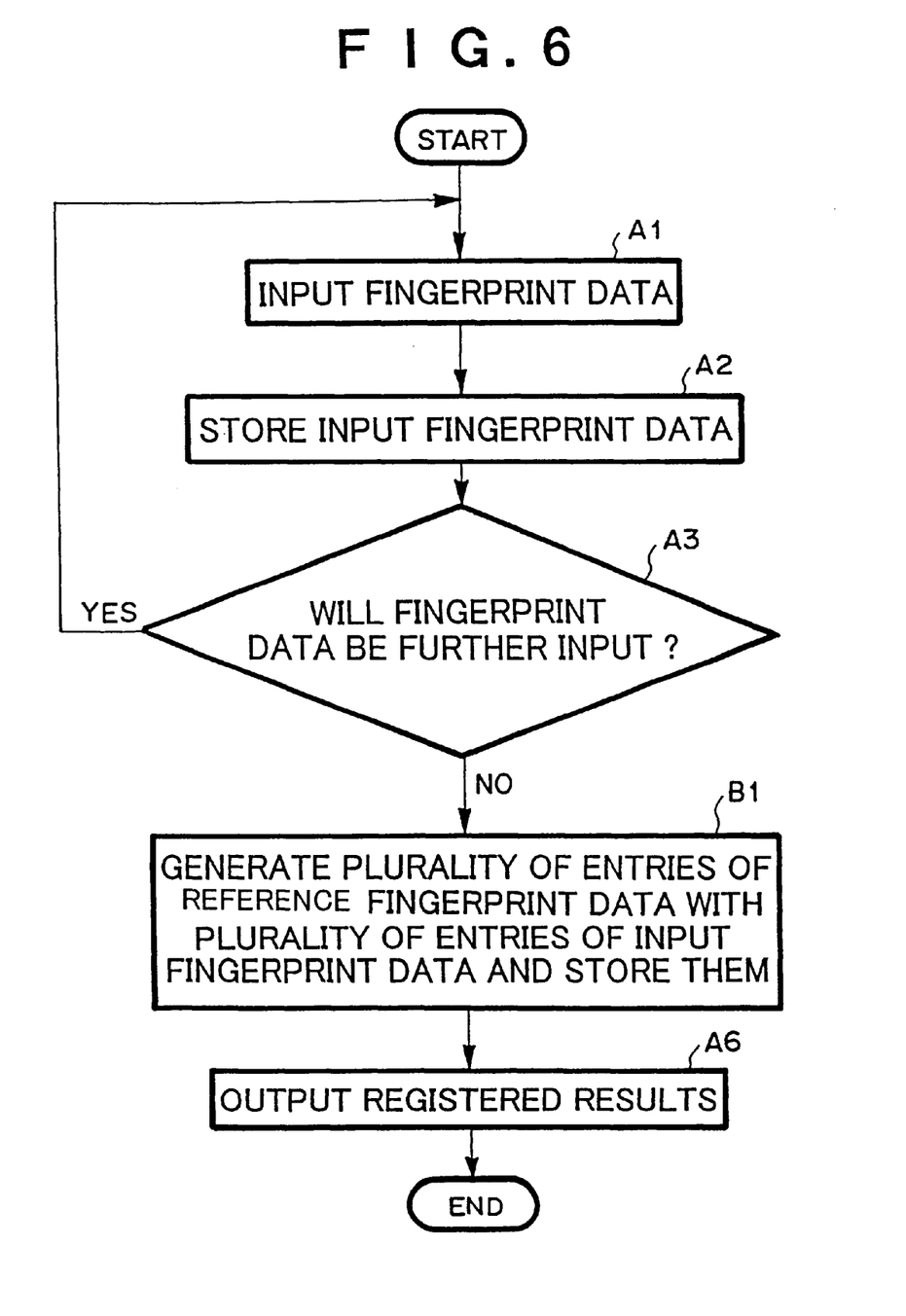
FIG. 6 is a flow chart showing a fingerprint data registering process according to the second embodiment of the present invention.
Figure 7:
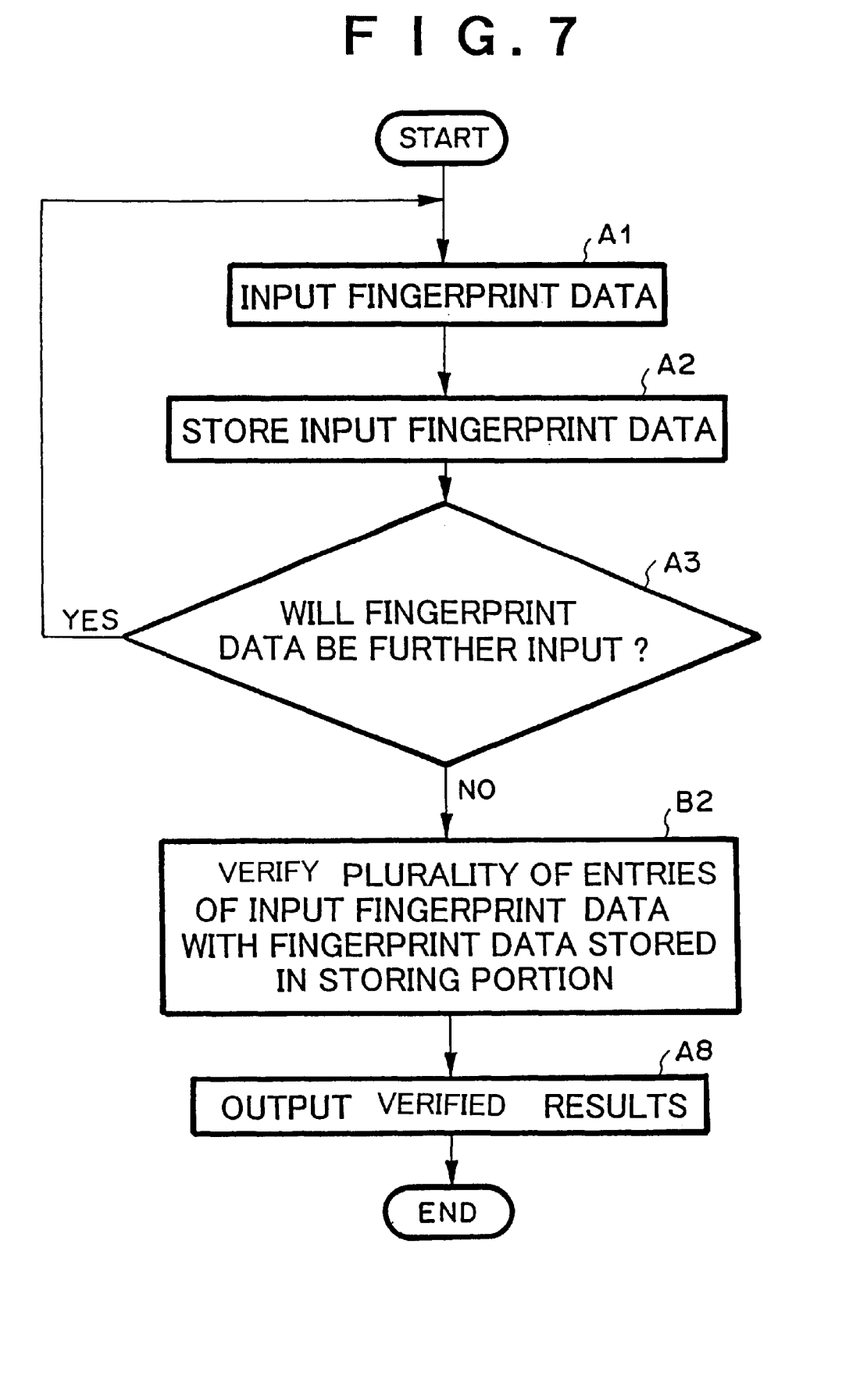
FIG. 7 is a flow chart showing a fingerprint data verifying process according to the second embodiment of the present invention.

Next, with reference to FIGS. 5, 6, and 7, the overall operation of the second embodiment of the present invention will be described. FIGS. 6 and 7 are flow charts showing processes of the second embodiment of the present invention.

With reference to FIGS. 5 and 6, the fingerprint data registering process will be described. In FIG. 6, steps A1 to A3 are the same as those shown in FIG. 2. For simplicity, their description is omitted. The switch SW connects the input device 1 to the multiple entry reference fingerprint data registration processing portion 51. Thus, the multiple entry reference fingerprint data registration processing portion 51 generates a plurality of entries of reference fingerprint data (of which feature points have been extracted) with all entries of fingerprint data stored in the multiple entry fingerprint data storing portion 31 and stores the generated fingerprint data to the multiple entry reference fingerprint data storing portion 61 (at step B1).

Next, with reference to FIGS. 5 and 7, the fingerprint data verifying process will be described. Since Steps A1 to A3 shown in FIG. 7 are the same as those shown in FIG. 3, their description is omitted. The switch SW connects the input device 1 to the multiple entry fingerprint data verification processing portion 52. The multiple entry fingerprint data verification processing portion 52 verifies a plurality of entries of input fingerprint data with a plurality of entries of fingerprint data stored in the multiple entry reference fingerprint data storing portion 61 (at step B2).

Figure 8:
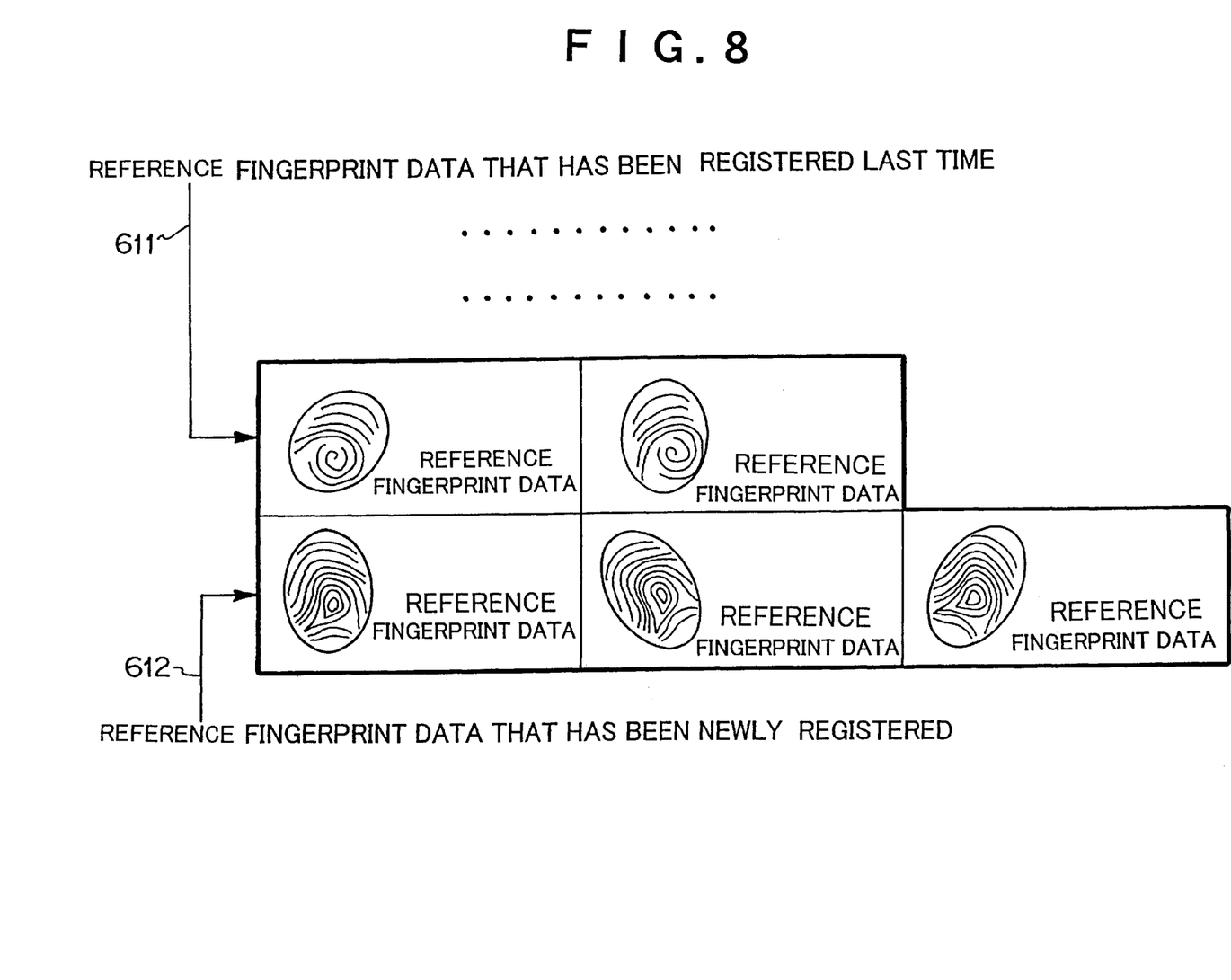
FIG. 8 is a schematic diagram showing images of fingerprints that have been registered and verified according to the second embodiment of the present invention.

Next, a real example of the second embodiment will be described. In this example, it is assumed that fingerprint data of a right index finger rotated at angles 0, −45, and ±45 in the order is input. The fingerprint data of the right index finger is successively stored to the multiple entry fingerprint data storing portion 31. The multiple entry fingerprint data verification processing portion 52 extracts feature points from the entries of the fingerprint data, generates three entries of reference fingerprint data, and stores the generated entries to the multiple entry reference fingerprint data storing portion 61 (at step B1). FIG. 8 shows reference fingerprint data 611 that has been registered last time in the multiple entry reference fingerprint data storing portion 61 and reference fingerprint data 612 that has been newly registered in the multiple entry reference fingerprint data storing portion 61.

When the fingerprint data verifying process is performed, the switch SW connects the input device 1 to the multiple entry fingerprint data verification processing portion 52. Likewise, assuming that fingerprint data of a right index finger rotated at angles of 0, −45, and +45 are input, the multiple entry fingerprint data verification processing portion 52 verifies the three entries of the input fingerprint data and the rotated angles thereof with those stored in the multiple entry reference fingerprint data storing portion 61.

According to the present invention, since a person is identified with rotated angles of fingerprint data and the rotated order thereof along with the fingerprint data, it becomes very difficult for a third party to forge fingerprint data and commit a fraud using the forged fingerprint data.

In addition, since fingerprint data to be verified is filtered using rotated angles of fingerprint data and a rotated order thereof, both the authenticating time of a person and the fingerprint verifying time can be shortened. Since only fingerprint data is input, a special input device other than a fingerprint scanner is not required. According to the present invention, since the security level can be improved with such a simple structure and a person can be physically identified, the authenticating ratio for a person according to the present invention is much higher than that according to a system using a secret key and a public key.

Although the present invention has been shown and described with respect to a best mode embodiment thereof, it should be understood by those skilled in the art that the foregoing and various other changes, omissions, and additions in the form and detail thereof may be made therein without departing from the spirit and scope of the present invention.

What is claimed is:

1. A fingerprint verifying method for authenticating a person, comprising the steps of:
   (a) having a user place a fingertip at a first angular position on an imaging area, scanning the fingertip of the user, and storing first fingerprint data corresponding to the scanned fingertip at the first angular position, along with first angular data indicating the first angular position, in a memory;
   (b) having a user place the fingertip at a second angular position on an imaging area, scanning the fingertip of the user, and storing second fingerprint data corresponding to the scanned fingertip at the second angular position, along with second angular data indicating the second angular position, in the memory, the second angular position being different from the first angular position;
   (c) having a person to be verified place a fingertip at the first angular position on the imaging area, scanning the fingerprint of the person to be verified, and comparing information corresponding to the scanned fingerprint at the first angular position with the stored first fingerprint data obtained from the memory;
   (d) having the person to be verified place the fingertip at the second angular position on the imaging area, scanning the fingerprint of the person to be verified, and comparing information corresponding to the scanned fingerprint at the second angular position with the stored second fingerprint data obtained from the memory; and
   (e) based on the comparisons made in steps (c) and (d), either verifying that the person to be verified corresponds to the user, or not verifying that the person to be verified corresponds to the user.

2. The fingerprint verifying method as set forth in claim 1, wherein the verification of the person to be verified is based in part on a first particular order in which the person to be verified places the fingertip at different angular directions on the imaging area having to match a second particular order in which the user placed the fingertip at the same different angular directions on the imaging area.

* * * * *